United States Patent [19]

Pedicano et al.

[11] Patent Number: 4,623,336
[45] Date of Patent: Nov. 18, 1986

[54] DISPOSABLE SAFETY NEEDLE SHEATH

[76] Inventors: James J. Pedicano, 222 N. Van Dien Ave., Ridgewood, N.J. 07450; James G. Kane, 3700 Oliver St. NW., Washington, D.C. 20015; Ernest Pedicano, 11 Hertford St., New Rochelle, N.Y. 10801

[21] Appl. No.: 609,343

[22] Filed: May 11, 1984

[51] Int. Cl.$^4$ .............................................. A61M 5/32
[52] U.S. Cl. ................................... 604/192; 604/263; 604/110
[58] Field of Search ............... 604/192, 263, 110, 111; 206/365, 571, 370, 366, 63.5

[56] References Cited

U.S. PATENT DOCUMENTS

| | | |
|---|---|---|
| 2,953,243 | 9/1960 | Roehr . |
| 3,021,942 | 2/1962 | Hamilton ........................ 604/192 X |
| 3,073,307 | 1/1963 | Stevens . |
| 3,074,542 | 1/1963 | Myerson . |
| 3,294,231 | 12/1966 | Vanderbeck . |
| 3,329,146 | 7/1967 | Waldman . |
| 3,333,682 | 8/1967 | Burke . |
| 3,367,488 | 2/1968 | Hamilton . |
| 3,434,473 | 3/1969 | Smith ............................. 604/192 X |
| 3,893,608 | 7/1975 | Koenig . |
| 3,934,722 | 1/1976 | Goldberg . |
| 4,113,090 | 9/1978 | Carstens . |
| 4,296,786 | 10/1981 | Brignola . |
| 4,332,323 | 6/1982 | Reenstierna . |
| 4,351,433 | 9/1982 | Elisha . |
| 4,375,849 | 3/1983 | Hanifl . |
| 4,452,358 | 6/1984 | Simpson . |

FOREIGN PATENT DOCUMENTS

| | | | |
|---|---|---|---|
| 113797 | 4/1969 | Denmark ............................ | 604/192 |
| 1240228 | 3/1967 | Fed. Rep. of Germany ...... | 604/192 |

Primary Examiner—John D. Yasko
Attorney, Agent, or Firm—Morgan & Finnegan

[57] ABSTRACT

A disposable safety needle sheath (10) has a funnel shaped receiving end (16) to protect the user's hand and guide a used needle into a sleeve (12). Retaining means (28, 30) within the sheath engage an inserted needle and a cap (18) seals the needle sheath after the used needle has been inserted and disengaged from a syringe (36). In the preferred embodiment of the invention, the retaining means comprises shoulders (28) at the open end of sleeve (12) to frictionally engage a needle hub (26), a cap (18) is mounted by a hinge to the receiving end (16), and locking means comprised of continuous annular ridge (32) and continuous annular groove (34) is provided to prevent the cap from being opened after closing.

27 Claims, 5 Drawing Figures

DISPOSABLE SAFETY NEEDLE SHEATH

TECHNICAL FIELD

This invention relates to the safe disposal of needles and, more particularly, to a safety sheath for disposal of an unsanitary needle without danger of injury or infection.

BACKGROUND AND OBJECTS OF THE INVENTION

Infection due to contact with unsanitary medical equipment has long posed a danger to personnel handling such equipment. Contact with used medical needles is particularly hazardous since needles are characteristically very sharp objects which can cause accidental wounds.

Previous attempts to provide safety sheaths have concentrated on preserving sterility of a packaged needle prior to use and on protecting the user against injury while fastening the sterile needle to a syringe. Examples of such structures can be found in U.S. Pat. No. 2,953,243 issued to Roehr for DISPOSABLE NEEDLE ASSEMBLY; U.S. Pat. No. 3,074,542 issued to Myerson for PACKAGE FOR HYPODERMIC NEEDLES; U.S. Pat. No. 3,294,231 issued to Vanderbeck for DENTAL NEEDLE SHIELD; U.S. Pat. No. 3,367,488 issued to Hamilton for HYPODERMIC SYRINGE PACKAGE; and U.S. Pat. No. 3,329,146 issued to Waldman for NEEDLE CONTAINER. Although some of the structures disclosed in these reference may also be used for disconnecting a used needle from a syringe for disposal, particularly Roehr '243, Vanderbeck '231 and Waldman '146, none of the structures disclosed provides adequate protection against injury to the hand of the user holding the sheath during reinsertion of a used needle.

Other previous attempts to provide needle sheaths which ensure sterility and provide protection against injury while fastening the needle to a syringe involve structures which must be partially destroyed to access the sterile needle. Examples of such structures, which do not provide any protection against injury or infection during disposal of the used, unsanitary needle, are found in U.S. Pat. No. 3,073,307 issued to Stevens for NEEDLE HUB AND SHEATH STRUCTURE; U.S. Pat. No. 3,333,682 issued to Burke for DISPOSABLE NEEDLE CONTAINER; and U.S. Pat. No. 3,934,722 issued to Goldberg for STERILE NEEDLE PACKAGE.

Infection even without direct contact with a used hypodermic needle also can be caused by atmospheric migration of bacteria. While some previous attempts have provided a sheath which may be used to disengage a used needle from a syringe, no structure has been provided which prevents bacteria migration. Examples of structures which allow bacteria migration after disposal of the used needle are found in U.S. Pat. No. 4,133,090 issued to Carstens for MEDICAL INSTRUMENT PACKAGE and Hamilton '488.

The only attempts to provide adequate protection against injury from direct contact with used hypodermic needles during disposal involve cannister-type containers. One such device utilizes sharp blades to sever a used needle from a syringe after it is inserted into an aperture in the cannister. Such a cannister suffers from several disadvantages. First, a cannister with blades is cumbersome and involves inconvenient transportation of the cannister itself or dangerous transportation of an exposed, used needle to the cannister. Second, the configuration of the cannister so as to contain many used needles necessarily involves a possibility that an infected needle may assume a position piercing the cannister, thereby exposing personnel handling the cannister to dangers of injury and infection by direct contact. Third, the requirement for an open aperture for inserting used needles permits undesirable bacteria migration which can also cause infection.

An improved cannister for used needle disposal is disclosed in U.S. Pat. No. 4,375,849 issued to Hanifl for SYRINGE NEEDLE REMOVAL AND DISPOSAL DEVICE. This patent discloses rim guards extending from the lid of the cannister over the user's hand providing protection during insertion of a used needle, a lid opening configured for disengaging the used needle from a syringe without blades, and a closable lid to retain used needles. However, this structure also suffers from several disadvantages overcome by the present invention. While the Hanifl '849 device is described as portable, carrying the cannister to an appropriate treatment station is inconvienient since it involves handling an additional piece of equipment. Moreover, since many needles are to be disposed of in a single cannister, carrying the cannister involves risk of injury from a previously inserted needle protruding through the cannister wall. If the Hanifl '849 device is accidentally upset with the lid in the open position, i.e., while in a position to receive additional needles, previously inserted, unsanitary needles may fall out of the cannister. Reinserting such spilled needles involves direct contact with the exposed needles, thereby increasing the risk of injury. Finally, the Hanifl lid must be reopened each time another used needle is inserted, allowing potentially infectious bacteria to migrate from previously inserted needles. This last disadvantage is aggravated by the portable nature of the device since the cannister will most likely be opened in the presence of patients being treated, exposing all involved to the danger of infection from bacteria migration.

It is therefore an object of this invention to provide a new and improved safety sheath for needles.

A further object of this invention is to provide a new and improved needle safety sheath which permits control over a needle without direct contact, particularly during removal from and insertion into the sheath.

A still further object of this invention is to provide, in a new and improved needle safety sheath, means for retaining a needle in the sheath.

A still further object of this invention is to provide a new and improved needle safety sheath which permits a used needle inserted therein to be disconnected from a syringe without direct contact and which does not permit the needle to become dislodged after such disconnection from a syringe.

Another object of this invention is to provide a new and improved needle safety sheath which protects the user from injuries due to needle contact during insertion of a needle into the sheath.

A still further object of this invention is to provide, in a new and improved needle safety sheath, means for guiding a needle into a sheath sleeve during insertion.

Another object of the present invention is to provide a new and improved needle safety sheath which prevents migration of bacteria from an unsanitary needle contained therein.

Another object of the present invention is to provide a new and improved needle safety sheath which does not permit access to an unsanitary needle contained therein.

A further object of the present invention is to provide a new and improved needle safety sheath package which is tamper-proof prior to use and which does not allow access to an unsanitary needle after use.

These and other highly desirable and unusual results are accomplished by the present invention in an economical structure which may be disposed of with confidence that no injury or infection from the unsanitary needle will result.

Objects and advantages of the invention are set forth in part herein and in part will be obvious herefrom, or may be learned by practice with the invention, the same being realized and attained by means of the instrumentalities and combinations pointed out in the appended claims.

The invention consists in the novel parts, constructions, arrangements, combinations, steps, and improvements herein shown and described.

SUMMARY OF THE INVENTION

In accordance with the present invention, a disposable safety needle sheath is provided to prevent direct contact with, and secure containment for, an unsanitary needle. Means for preventing migration of infectious bacteria from the unsanitary needle are also provided.

The disposable safety needle sheath in accordance with the present invention prevents accidental contact with an unsanitary needle during insertion and urges the unsanitary needle into a durable sheath sleeve. An additional advantage of the present invention is that a needle inserted into the sleeve is frictionally engaged, allowing the needle to be disconnected from a syringe without direct contact and preventing accidental dislodging of the needle from the sleeve after the syringe has been disconnected. Means for sealing the sheath after insertion of a used needle are provided.

In a preferred embodiment of the invention a durable sleeve closed at one end and attached at the open end to the lesser diameter of a funnel-shaped receiving end is provided. The funnel-shaped receiving end protects the user's hand and urges the used needle into the sleeve during insertion of a needle into the sheath. Means for frictionally engaging and retaining a needle in the sleeve are also provided. A cap to seal the open end of the sheath having a hinge attached to the receiving end is provided. In the preferred embodiment of the invention the cap lockingly engages the receiving end when closed, making it virtually impossible to reopen the sheath without destroying both the sheath and needle.

The retaining means holds the needle within the durable narrow sleeve in a position away from the closed end of the sleeve such that the needle cannot assume a position penetrating and protruding through the sleeve. The retaining means also prevents a needle held in the sleeve from accidentally falling out of the sheath.

The wide aperture of the receiving end protects the user's hand gripping the sleeve during removal or insertion of a needle by overlapping and covering that portion of the hand surrounding the sleeve. The funnel shape of the receiving end surprisingly forces a sterile needle being removed from the sheath away from the user's hand holding the sheath and also guides a needle being inserted toward the narrow sleeve aperture.

The cap seals the open end of the sheath to prevent bacteria migration and to provide further protection against the possibility of a needle falling out.

In the preferred embodiment of the invention the locking cap effectively prevents all access to the used needle. After closing, access can only be gained by compromising the structural integrity of the sheath. However, the sheath is constructed of durable materials which make it virtually impossible to compromise the sheath without also impairing the structure of a needle contained therein.

The hinge prevents the cap from being misplaced with respect to the other sheath components.

In use, the sheath may be sealed within a tamper-proof package with a sterile needle held therein by the retaining means and, unusually, with the locking cap in an open position. The tamper-proof package is opened and the tip of a syringe inserted into the open end of the sheath to access the needle. Of course, a syringe could alternatively be provided in a package with the sheath and sterile needle. The syringe rotationally mates with the needle hub and is removed with the needle mounted thereon by a lateral pulling action. During this removal the funnel shape of the receiving end guides the needle tip away from the hand gripping the sleeve, thereby preventing accidental injury during removal. After use the needle is inserted into the sheath while still mounted on the syringe. The wide aperture of the receiving end prevents accidental pricking of the hand and the funnel shape guides the needle into the sheath sleeve. Thus, the funnel shape of the receiving end surprisingly protects the user's hand during both removal and insertion of the needle. The inserted needle engages the retaining means and the syringe is disengaged for separate disposal. The frictional engagement of the needle with the retaining means prevents the needle from falling out of the sleeve prior to closing the cap. Closing the cap seals the sheath to prevent migration of bacteria from the used needle through the atmosphere.

In the preferred embodiment wherein the cap locks and cannot be reopened without compromising the structure of both the sheath and needle, the surprising result of denying all access to the used needle is obtained. Thus, the sheath cannot accidentally open to allow bacteria to migrate or to allow the needle to fall out. Moreover, even if the sheath was reopened the retaining means would prevent the needle from falling out. The locked cap obtains the remarkable result of denying access to those who seek entry, whether it be medical personnel who mistakenly believe that a sterile needle is contained therein or drug abusers seeking intact needles regardless of sterility. Thus sealed, the sheath can be disposed of with confidence that the used needle contained therein presents no danger to anyone.

It will be apparent from the foregoing general description that the objects of the invention specifically enumerated herein are accomplished by the invention as here embodied Thus, as one advantage of the present invention, a needle may be advantageously removed from and inserted into a needle safety sheath with no direct needle contact, resulting in surprising confidence that no needle injury will result.

As a further advantage of the present invention, bacteria from the unsanitary needle is prevented from migrating through the atmosphere.

As yet a further advantage of the present invention all access to the interior of the safety sheath is effectively denied once the cap is sealed. This unexpected denial of access to the sheath may be combined with the attributes of a tamper-proof package to achieve the remarkable combination of assuring sterility of the needle prior to use and effectively preventing injury and infection before, during and after use.

It will be understood that the foregoing general description and the following detailed description as well are exemplary and explanatory of the invention but are not restrictive thereof.

BRIEF DESCRIPTION OF THE DRAWINGS

The accompanying drawings, referred to herein and constituting a part hereof, illustrate preferred embodiments of the product of the present invention, and together with the description serve to explain the principles of the invention, in which.

DESCRIPTION OF THE PREFERRED EMBODIMENTS

Figure 1:
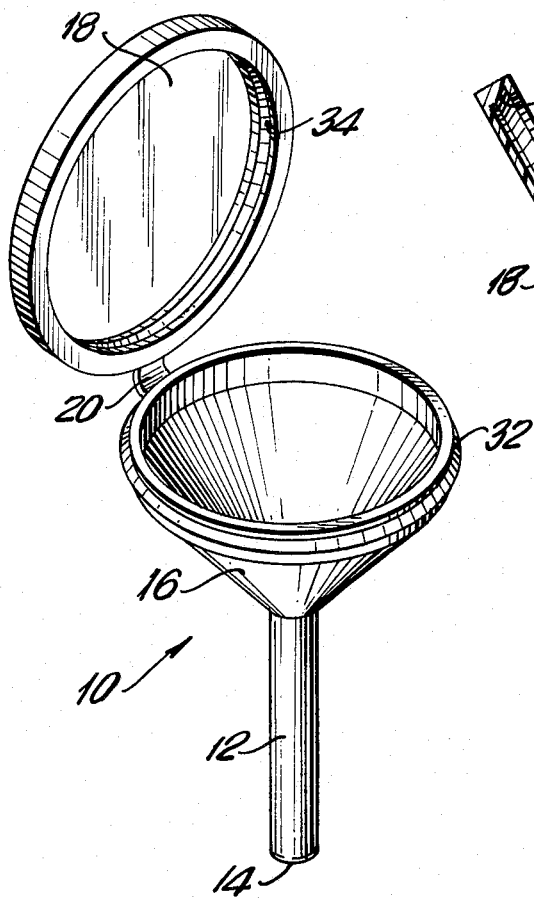
FIG. 1 is a perspective view of a disposable safety needle sheath constructed in accordance with the first preferred embodiment of the invention with the cap in an open position.

Referring now more particularly to FIGS. 1–4 of the accompanying drawings, there is illustrated a first preferred embodiment of a safety sheath constructed in accordance with the present invention, indicated generally by reference numeral 10. As here embodied, sheath 10 includes a stiff, durable sleeve 12 having a closed end 14 and an opposite open end integral with the small open end of a funnel-shaped receiving guide 16. A hinge 20 connects the receiving guide to a cap 18 for sealing the open end of sheath 10.

Sleeve 12, including the open end thereof, and the small open end of funnel-shaped receiving guide 16 are dimensioned to receive a longitudinally inserted needle and are, typically, on the order of one-eighth to one-quarter of one inch in diameter. Retention of the needle within the sleeve is obtained by frictional engagement of the needle with a narrower sleeve diameter provided by frictional surfaces 30, or by engagement of a tapered needle hub 26 with the open end of the sleeve. Rotational movement of the inserted needle relative to the sleeve is prevented by the engagement of inward flanges 42 in sleeve 12 with the outward flanges which are commonly provided on needle hubs.

The wide aperture of funnel shaped receiving guide 16 is sufficiently large to provide a large target for insertion of a needle and to cover the user's fingers gripping sleeve 12. The diameter of the wide aperture is preferably greater than one inch in order to provide a sufficiently large protective target for insertion and may be as large as three inches in order to fully cover the user's hand. The added protection of a diameter greater than three inches is minimal in relation to the inconvenience in handling such a large aperture sheath.

The configuration of funnel shaped receiving guide 16 is such that a needle inserted within the wide aperture of receiving guide 16 is urged by the pitch of the funnel shape towards the small open end of the receiving guide into sleeve 12. The pitch of the funnel shape must be balanced against the convenience in handling the sheath, which makes minimizing the funnel height necessary to reach the chosen wide aperture desirable. It has been found that funnel shapes with interior angles of 80 to 140 degrees provide an adequate balance of the height to width, with interior funnel angles of 100 to 120 degrees providing desirable funnel pitch at acceptable funnel heights.

A cap 18 for sealing the open end of sheath 10 is attached to receiving guide 16 by a hinge 20. Cap 18 and receiving guide 16 are provided with locking means to prevent the sheath from being reopened after a used needle is inserted and the cap closed. As here embodied, the receiving guide is provided with a stiff annular ridge 32 to engage a recess or groove 34 on cap 18. The lip of cap 18 distorts slightly as the cap is forced over the upper slanted surface of annular ridge 32. Distortion of the cap lip results from either the use of a less rigid material than the annular ridge to form the cap lip or from the inherently weaker structure of the cap lip caused by the presence of the groove. The resilient cap resumes its natural position once the groove fully engages the annular ridge so that the flat, lower surfaces of annular ridge 32 and groove 34 come into a face to face relationship when the cap is fully closed. This facing relationship of the flat surfaces of the annular ridge and groove locks the cap in the fully closed position so it cannot easily be removed. The face to face relationship of these lower flat surfaces locks the cap closed since application of an upward force relative to said sheath merely presses these surfaces closer together, preventing the closed cap from opening. Preferably, the plane formed by the face to face flat surfaces is perpendicular to the axis of the sleeve, but at the very least the flat lower surface of annular ridge 32 must not be slanted so that upward force on cap 18 causes the same type of resilient distortion as occurs while the cap is forced closed over the upper slanted edge of annular ridge 32. As thus constructed the sheath, once closed, is tamper-proof and cannot readily be opened without the use of an external tool.

Advantageously sleeve 12, receiving guide 16, and cap 18 are all made of a stiff, lightweight material which is sufficiently rigid to prevent accidental piercing with a needle and to make improper opening after engagement of the locking closure virtually impossible. Preferably, all of these surfaces are made of a stiff durable polystyrene or polyester or copolymer thereof. Hinge 20 may be made of any material which is sufficiently flexible to allow cap 18 to move freely relative to the receiving guide without becoming disconnected therefrom.

Figure 3:
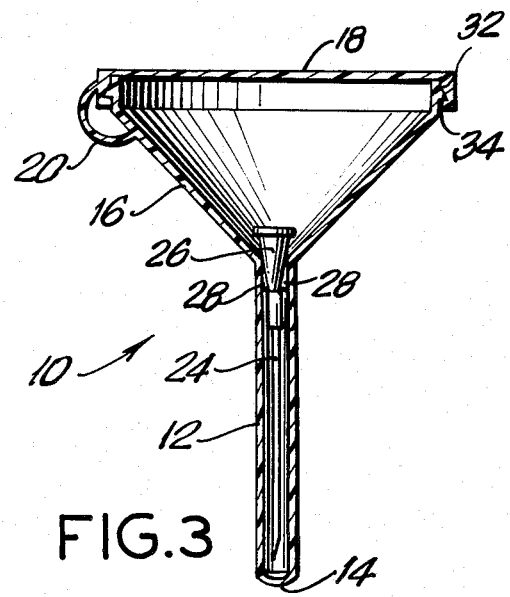
FIG. 3 is an axial, cross-section elevation view of the sheath structure of FIG. 1, and illustrating a used needle disposed in the sheath and the cap in the closed, locked postion.
Figure 4:
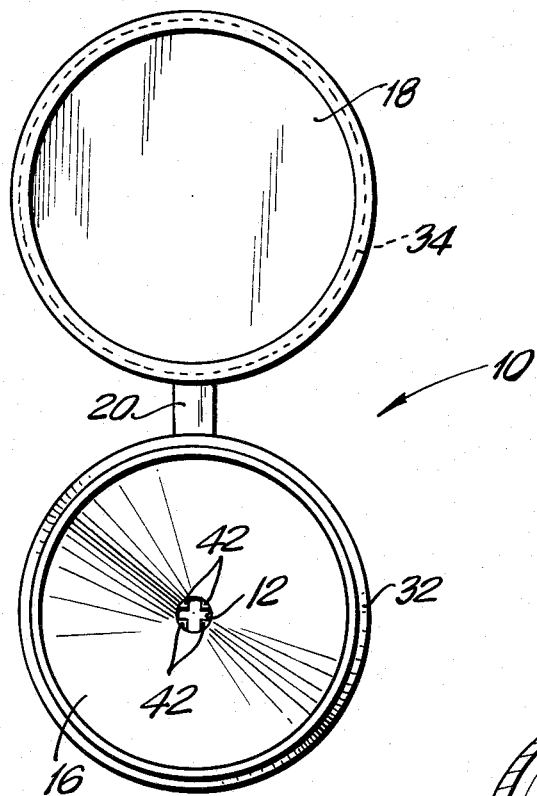
FIG. 4 is a top plan view of the sheath structure of FIG. 1.
Figure 5:
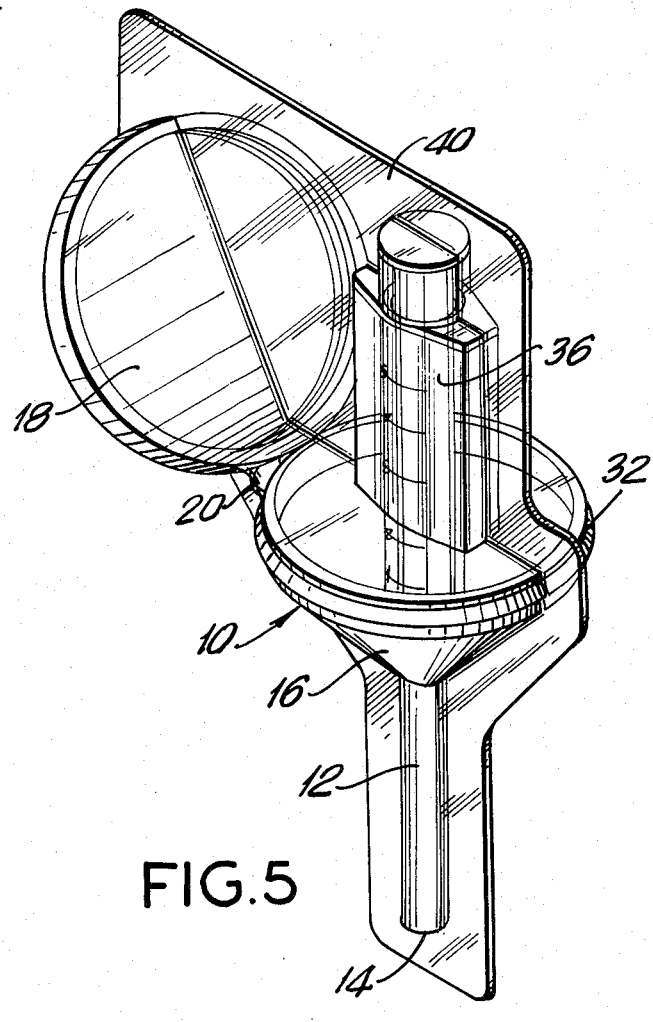
FIG. 5 is a perspective view of the second preferred embodiment of the invention disposed in a tamper-proof package as part of a kit including a sterile hypodermic needle and syringe.

In a second preferred embodiment of a safety sheath constructed in accordance with the present invention and shown in FIG. 5 with reference numerals common to FIGS. 1–4, a sterile needle is prepackaged and frictionally held in the sleeve with the cap in the open position, all sealed in a tamper-proof package. FIG. 5 shows an optional syringe 36 prepackaged with sheath 10 attached to the sterile needle. The tamper-proof package is a vacuum sealed envelope 40 of suitable flexible sheet wrapping such as cellophane, foil or plastic wrap which preserves sterility and allows determination of whether the sterility of the contents has been compromised by visual inspection. The tamper-proof package is opened to access the sterile needle and optional syringe for use. The used needle is reinserted into the sheath, disconnected from the syringe, and sealed in the sheath by closing the locking cap.

FIG. 1 illustrates a safety needle sheath 10 constructed in accordance with the invention having sleeve 12 with closed end 14 and an opposite open end attached to the small open end of funnel shaped receiving guide 16. The wide aperture of receiving guide 16 is distal to sleeve 12 and is configured as discussed above to cover and protect fingers gripping sleeve 12. Cap 18 is shown connected to receiving guide 16 via living hinge 20. Hinge 20 is preferably formed to position the cap ready for use and to allow closing in a simple, one-handed fashion.

Figure 2:
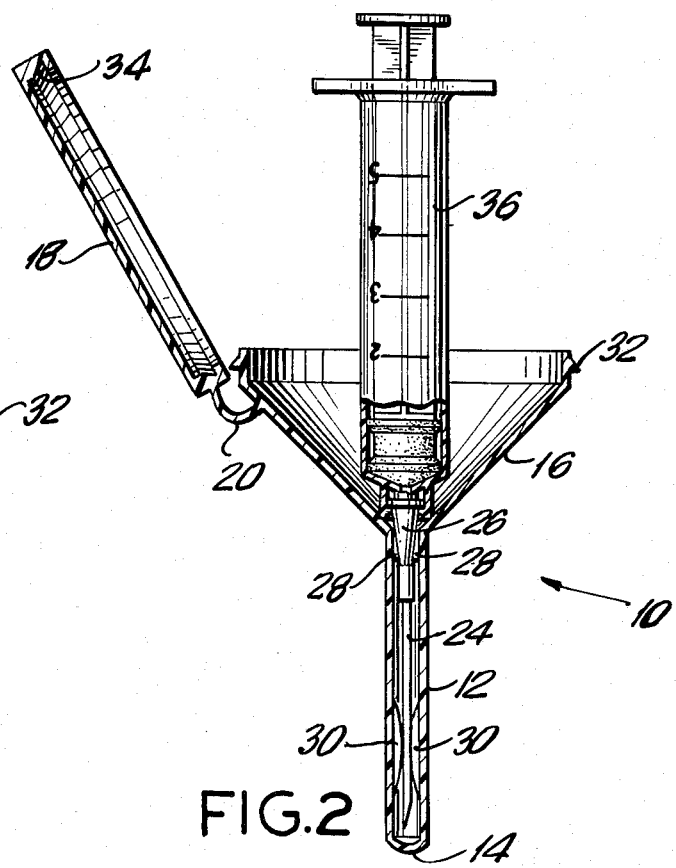
FIG. 2 is an axial, cross-section elevation view of the sheath structure of FIG. 1, and also illustrating a needle attached to a syringe inserted in the sheath and frictionally held both along the shaft of the needle and at the needle hub.

FIG. 2 is an axial cross-section view of the preferred embodiment of the invention, showing sheath 10 with a needle 24 attached to a syringe 36. The position shown in FIG. 2 can occur prior to removal of a sterile needle and syringe from the sheath or after insertion of a used needle into the sheath but prior to disconnection of the syringe from the needle The interaction of inward flanges 42 (See FIG. 4) and protrusions on needle hub 26 (not shown) prevent rotation of the needle relative to the sheath and permit rotation of syringe 36 relative to needle hub 26 to disengage the needle from the sytinge. Needle 24 is lodged in sleeve 12 by the frictional engagements of tapered needle hub 26 with shoulders 28 at the open end of sleeve 12 or, alternatively, by engagement of needle 24 with the tapered, frictional surfaces 30 (shown by broken lines) which create a narrow sleeve diameter relative to the needle. The frictional engagement of needle 24 with frictional surfaces 30 or of tapered needle hub 26 with shoulders 28 holds the needle securely in the sleeve after the syringe is disconnected for separate disposal. The needle so held does not contact closed end 14 of sleeve 12. Cap 18 is shown in the open, unlocked position attached to receiving guide 16 by hinge 20. Sleeve 12, receiving guide 16, and shoulders 28 or, alternatively, frictional surfaces 30 are preferably formed as a single unit. Hinge 20 can also be formed as part of the single unit to provide a sheath which is a single integral body.

FIG. 3 shows the preferred embodiment of the invention with needle hub 26 frictionally engaging shoulders 28 to firmly hold needle 24 within sleeve 12. Cap 18 is in the closed, locking position with annular ridge 32 on receiving guide 16 engaging the corresponding recess or groove 34 in cap 18. Annular ridge 32 and groove 34 are shown in exaggerated detail in the figures to illustrate their interaction. As previously discussed and shown in FIG. 3, cap 18 mounts over the wide aperture of receiving guide 16 with the flat, lower surfaces of the annular ridge and groove assuming a face to face relationship, effectively preventing the cap from being reopened. Upward pressure on the cap relative to the receiving guide merely forces the flat surfaces of the annular ridge and groove more closely against one another and will not open the sheath.

FIG. 4 is a top plan view of sheath 10 illustrating the relationship between receiving guide 16 and sleeve 12, showing cap 18 in a fully open position adjacent to receiving guide 16. Annular ridge 32 and groove 34 are preferably continuous around the rims of receiving guide 16 and cap 18, respectively, as shown. Inwardly extending flanges 42 engage corresponding ridges on needle hub 26, as discussed above in relation to FIG. 2, to provide counter-rotational force during connection and disconnection of the syringe from the needle. This manner of engaging a syringe and needle is currently available in products from Becton Dickinson and Company.

FIG. 5 shows sheath 10 in a second preferred embodiment sealed within a tamper-proof sterile package 40 as part of a kit including a hypodermic syringe 36 and needle (not visible) positioned in the sheath in a manner similar to that shown in FIG. 2. In FIG. 5 sheath 10 is shown sealed in sterile envelope 40 with locking cap 18 in the open position. Tamper-proof envelope 40 preserves the sterility of the needle frictionally held in sleeve 12 and also of the optional hypodermic syringe attached to the needle hub.

In use, tamper-proof, sealed envelope 40 is opened to access the sterile needle held in sleeve 12. The tamper-proof package cannot be resealed and therefore provides visual evidence of previous opening and, therefore, of sterility. When not included in the kit a syringe is rotationally coupled with the needle hub 26 (See FIG. 2) and both needle 24 and syringe 36 are removed from the sheath by a lateral pulling action. Syringe 36 and sterile needle 24 are then ready for use.

After use, needle 24 is reinserted into sheath 10. The wide aperture of receiving guide 16 provides protection during reinsertion by covering the area of the user's hand gripping sleeve 12 to hold the sheath. The wide aperture also provides a broad target area for reinsertion (See FIG. 4) of the needle. The funnel shape of receiving guide 16 facilitates reinsertion by guiding the needle toward the small open end of receiving guide 16 and, therefore, into the open end of sleeve 12, thereby preventing injury which could otherwise result if the needle were to stray outside the wide aperture. Longitudinal force is applied to frictionally engage needle hub 26 with shoulders 28 or, alternatively, needle 24 with tapered frictional surfaces 30. Syringe 36 is easily disconnected from needle hub 26 for separate disposal by rotating the syringe relative to the sheath. Rotation of needle 24 relative to sleeve 12 is prevented by the engagement of inwardly extending flanges 42 with outwardly extending flanges on the needle hub. Such outwardly extending flanges are provided on needle hubs currently available from Becton Dickinson and Company. Sheath 10, with needle 24 frictionally retained in sleeve 12, is sealed by closing cap 18 into the locked position shown in FIG. 3 and is not easily reopened due to the positive, locking engagement of annular ridge 32 with groove 34. This locking engagement is a particularly important feature of the present invention since sheath 10 cannot be reopened by medical personnel mistakenly believing that the needle contained therein is sterile and ready for use. The locking cap also provides additional protection against accidental dislodging of the used needle from the syringe and prevents accidental opening of the sheath which would allow infectious bacteria to migrate through the environment. Finally, since access to the closed sheath can only be gained by virtually destroying both the sheath and needle, drug abusers cannot easily obtain intact, unsanitary needles. Hinge 20 keeps cap 18 attached to receiving guide 16 in a position ready for closing to assure that the abovementioned desirable features are not forfeited due to the cap being misplaced.

In the sealed, locked position shown in FIG. 3 Sheath 10 allows disposal of an unsanitary needle with complete confidence that neither the person reinserting the needle nor any person subsequently handling the sheath will be exposed to injury or infection from either direct contact with or bacteria migrating from the used needle. Since only one needle is disposed of in the novel safety sheath there is no danger of needles piercing or falling out of a cannister, or of bacteria migrating when a cannister is opened to insert additional needles. There is also no danger of drug abusers obtaining intact, unsanitary needles by simply reopening a cannister. The preferred packaging of the sheath with a sterile needle in a tamper-proof envelope (See FIG. 5) provides a convenient method of packaging a sterile needle in close association with a safety disposal sheath constructed in accordance with the present invention.

To the extent not already indicated, it also will be understood by those of ordinary skill in the art that any one of the various specific embodiments herein described and illustrated may be further modified to incorporate features shown in other of the specific embodiments, as desired.

The invention in its broader aspects therefore is not limited to the specific embodiments herein shown and described but departures may be made therefrom within the scope of the accompanying claims, without departing from the principles of the invention and without sacrificing its chief advantages.

We claim:

1. A disposable safety needle sheath for disposal of a used or otherwise unsanitary needle comprising:
    sleeve means closed at one end thereof and open at the opposite end thereof for receiving a used, unsanitary needle inserted therein,
    needle retaining means within said sleeve means for grasping and holding a used, unsanitary needle inserted into said sleeve means;
    wide aperture needle receiving means communicating with the open end of said sleeve means for subtantially covering and protecting the fingers of a user grasping said sleeve means and for guiding a used, unsanitary needle towards the open end of said sleeve means;
    sheath closure means for closing the open end of said sleeve means after a used, unsanitary needle has been inserted into said sleeve means; and
    means for substantially preventing said sheath closure means from being reopened after said sheath closure means has assumed the closed position closing the open end of said sheath, thereby preventing access to said used, unsanitary needle contained in said sheath.

2. The disposable safety needle sheath as in claim 1 wherein said wide aperture needle receiving means is funnel shaped and the small opening thereof is integral with the open end of said sleeve means.

3. The disposable safety needle sheath as in claim 2 wherein said needle retaining means frictionally engages the shaft of a needle inserted into said sleeve means.

4. The disposable safety needle sheath as in claim 3 wherein said needle retaining means comprises tapered frictional surfaces integral with said sleeve means locally reducing the diameter of said sleeve means.

5. The disposable safety needle sheath as in claim 2 wherein said needle retaining means comprises shoulders integral with said sleeve means at the open end thereof to frictionally engage the hub of a needle inserted into said sleeve means.

6. The disposable safety needle sheath as in claim 5 further comprising hinge means connecting said sheath closure means to said receiving means.

7. The disposable safety needle sheath as in claim 6 wherein said sleeve means, needle retaining means, receiving means and sheath closure means all comprise a durable, substantially puncture-proof material.

8. The disposable safety needle sheath as in claim 7 wherein said sleeve means, needle retaining means, receiving means, hinge and sheath closure means are all formed as a single body.

9. The dispoable safety needle sheath as in claim 7 wherein said durable, puncture-proof material is polystyrene.

10. A tamper-proof disposable safety needle sheath for disposal of a used or otherwise unsanitary needle, comprising:
    sleeve means closed at one end thereof and open at the opposite end thereof for receiving a used, unsanitary needle inserted therein;
    needle retaining means within said sleeve means for grasping and holding a used, unsanitary needle inserted into said sleeve means;
    wide aperture needle receiving means communicating with the open end of said sleeve means for guiding a used, unsanitary needle toward the open end of said sleeve means and for substantially covering and protecting a user's fingers grasping said sleeve means,
    a cap assuming a first, open position and a second closed position, said cap effectively sealing the open end of the safety needle sheath in said second position after a used, unsanitary needle has been inserted into said sleeve means; and
    locking means positively engaging said cap and said needle receiving means for substantially preventing said cap from being reopened after assuming said second, closed position without use of an external tool, thereby preventing access to said used unsanitary needle contained in the sheath.

11. The dispoable safety needle sheath as in claim 10 wherein said locking means comprises a relatively stiff continuous annular ridge on said wide aperture needle receiving means and a corresponding continuous annular groove in said cap, said cap groove and said annular ridge assuming a first, unlocked position when said cap is in said first, open position and a second, locked position when said cap is in said second, closed position.

12. The disposable safety needle sheath as in claim 11 wherein said needle receiving means is funnel shaped and the small open end thereof is integral with the open end of said sleeve means.

13. The disposable safety needle sheath as in claim 11 wherein said relatively stiff annular ridge includes:
    a top slanted surface grandually increasing in diameter from a first point on said receiving means adjacent to the open end of said sheath to a maximum annular ridge diameter at a point longitudinally displaced away from said open end of said sheath; and
    a bottom surface connecting said maximum annular ridge diameter point to said receiving means at a second point on said receiving means longitudinally displaced away from said sheath opening at a distance not greater than the longitudinal distance from said open end of said sheath to said maximum annular ridge diameter point.

14. The disposable safety needle sheath as in claim 13 wherein a portion of said continuous annular groove is in face to face relationship with said annular ridge bottom surface when said annular groove and annular ridge assume said second, locked position, said stiff annular ridge substantially preventing said snnular groove from being removed from said face to face relationship with said annular ridge bottom surface.

15. The disposable safety needle sheath as in claim 14 wherein said face to face relationship lies in a plane perpendicular to the axis of said sheeve means.

16. A disposable safety needle sheath as in claim 15 wherein said needle retaining means frictionally engages the shaft of a needle inserted into said sleeve means.

17. A disposable safety needle sheath as in claim 16 wherein said needle retaining means comprises tapered surfaces integral with said sleeve means locally reducing the diameter of said sleeve means.

18. A disposable safety needle sheath as in claim 15 wherein said needle retaining means comprises shoulders integral with the open end of said sleeve means to frictionally engage the hub of a needle inserted into said sleeve means.

19. A disposable safety needle sheath as in claim 18 further comprising hinge means connecting said cap to said needle receiving means.

20. A disposable safety needle sheath as in claim 19 wherein said sleeve means, retaining means, needle receiving means, cap, and locking means all formed from a durable, puncture-proof material.

21. A disposable safety needle sheath as in claim 20 wherein said durable, puncture-proof material is polystyrene.

22. The disposable needle sheath as in claim 21 further comprising a tamper-proof sterile package enveloping said disposable needle sheath.

23. The disposable safety needle sheath in accordance with claim 1 wherein said means for substantially preventing said sheath closure measn from being reopened further comprise:

annular groove means on said sheath closure means; and stiff annular ridge means on said wide aperture needle receiving means for resiliently engaging said annular groove means as said sheath closure means is urged into said closed position closing the open end of said sheath and for firmly resisting and substantially preventing said sheath closure means from being reopened.

24. The dispoable safety needle sheath as in claim 1 further comprising a needle disposed within said sleeve means.

25. The disposable safety needle sheath as in claim 12 further comprising a needle disposed within said sleeve means.

26. A method for disposing of a used, unsanitary needle comprising the following steps performed in the order set out below;
  (i) inserting a used, unsanitary needle into a disposable safety needle sheath having
    (a) sleeve means closed at one end thereof and open at the opposite end thereof for receiving said used, unsanitary needle inserted therein,
    (b) needle retaining means within said sleeve means for grasping and holding said used, unsanitary needle inserted into said sleeve means,
    (c) wide aperture needle receiving means communicating with the open end of said sleeve means for substantially covering and protecting the fingers of a user grasping said sleeve means and for guiding said used, unsanitary needle towards the open end of said sleeve means,
    (d) a cap assuming a first, open position and a second, closed position, said cap effectively sealing the open end of said safety needle sheath in said second, closed position after a used, unsanitary needle has been inserted into said sleeve means, and
    (e) locking means positively engaging said cap and said needle receiving means for substantially preventing said cap from being reopened from said second, closed position without use of an external tool;
  (ii) closing said cap after said used, unsanitary needle has been inserted into said disposable safety needle sheath; and
  (iii) engaging said locking means to prevent said cap from being reopened to obtain access to said used, unsanitary needle contained in aid disposable safety needle sheath.

27. The method of disposing of a used, unsanitary needle according to claim 26, wherein said used, unsanitary needle is inserted into said disposable safety needle sheath while attached to a syringe, said syringe being disconnected from said needle before closing said cap.

* * * * *